(12) United States Patent
Feitsma et al.

(10) Patent No.: US 9,005,896 B2
(45) Date of Patent: Apr. 14, 2015

(54) METHOD FOR AMPLIFYING NUCLEIC ACIDS

(75) Inventors: Harma Feitsma, Eindhoven (NL);
Marlieke Overdijk, Eindhoven (NL);
Anja Van De Stople, Eindhoven (NL);
Pieter Jan Van Der Zaag, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 120 days.

(21) Appl. No.: 13/818,325

(22) PCT Filed: Aug. 31, 2011

(86) PCT No.: PCT/IB2011/053817
§ 371 (c)(1),
(2), (4) Date: Feb. 22, 2013

(87) PCT Pub. No.: WO2012/029037
PCT Pub. Date: Mar. 8, 2012

(65) Prior Publication Data
US 2013/0210008 A1 Aug. 15, 2013

(30) Foreign Application Priority Data
Sep. 1, 2010 (EP) .................................... 10174857

(51) Int. Cl.
*C12Q 1/68* (2006.01)
*C12P 19/34* (2006.01)

(52) U.S. Cl.
CPC ............ *C12Q 1/6869* (2013.01); *C12Q 1/6837* (2013.01); *C12Q 1/6874* (2013.01)

(58) Field of Classification Search
CPC .. C12Q 1/6844; C12Q 1/6853; C12Q 1/6869; C12Q 1/6873; C12Q 1/6874; C12Q 2525/00; C12Q 2525/30; C12Q 2525/301; C12Q 2565/501; C12Q 2565/537
See application file for complete search history.

(56) References Cited

U.S. PATENT DOCUMENTS

| 6,300,070 B1 | 10/2001 | Boles et al. |
| 7,115,400 B1 | 10/2006 | Adessi et al. |
| 2009/0117573 A1* | 5/2009 | Fu et al. .............................. 435/6 |
| 2009/0226975 A1 | 9/2009 | Sabot et al. |
| 2011/0311975 A1 | 12/2011 | Van De Stolpe et al. |

FOREIGN PATENT DOCUMENTS

| DE | 10051564 | 8/2002 |
| EP | 2426214 | 3/2012 |
| WO | WO0063695 | 10/2000 |
| WO | WO0148184 | 7/2001 |

(Continued)

OTHER PUBLICATIONS

Braeckmans, et al., (2003) Nature Materials 2, 169-173.

(Continued)

*Primary Examiner* — Young J Kim

(57) ABSTRACT

The present invention describes methods for amplifying a target nucleic acid wherein target nucleic acids hybridize to capture probe nucleic acids which are immobilized to a support via their 5' end. The hybridization product is further extended with a polymerase to form a double stranded nucleic acid. To this double stranded nucleic acid, a hairpin nucleic acid is ligated. This ligation product is further amplified and sequenced.

15 Claims, 6 Drawing Sheets

(56) References Cited

FOREIGN PATENT DOCUMENTS

| WO | WO0175154 | 10/2001 |
| WO | WO0233419 | 4/2002 |
| WO | WO2007115815 | 10/2007 |

OTHER PUBLICATIONS

Jain (2003) Expert Rev. Mol. Diagn. 3, 153-161.
Ju et al (2006) Proc. Natl. Acad. Sci. USA, 103, 19635-19640.
Lehmann (2002) Nature Materials 1, 12-13.
Margulies, et al., (2005) Nature 437, 376-380.
Okou, et al., (2007) Nat. Methods 4, 907-909.
Shapero, et al., (2001) Genome Res. 11, 1926-1934.
Walker, et al., (1992) Proc. Natl. Acad. Sci. USA 89; 392-396.
Porrect, et al., (2006), Current Protocols in Molecular Biology, XX, XX, pp. 7.8.1-7.8.22.
Westin, et al., (2000) Nat. Bioltechnol. 18, 199-204.
Kawasaki (2006) J. Biom. Techniques 17, 200-206.

* cited by examiner

METHOD FOR AMPLIFYING NUCLEIC ACIDS

FIELD OF THE INVENTION

The invention relates to the hybridization of target nucleic acids from a sample to a capture nucleic acid on a solid support and to the amplification of the hybridized target nucleic acid.

BACKGROUND OF THE INVENTION

The $2^{nd}$ generation sequencing technologies of Illumina Solexa, AB SOLiD and Roche 454 achieve their high throughput and relatively low costs per sequenced base by operating in a massively parallel fashion. They create many random fragments of the total input DNA, amplify each fragment separately on a bead or on an array, read out the sequences of those in a single flow cell, and are able to detect mutations only by matching all individual reads to a reference genome sequence (Margulies M. et al. (2005) Nature 437, 376-380). This way of operation has the drawback that many irrelevant parts of the genome are sequenced as well. This will especially be true for clinical sequencing, were usually sets of only tens to hundreds of genes are relevant for a diagnosis. Therefore, different technologies are currently in use to select relevant parts of the genomic DNA prior to introducing the sample to the sequencer. Most commonly, the DNA is hybridized to capture probes on a microarray that specifically bind the relevant parts. In a second step, the unbound, irrelevant parts are washed away, and subsequently the bound fragments are eluted and prepared to be loaded into the sequencer (Okou D. et al. (2007) Nat Methods 4, 907-909). Typically, target fractions of 0.1%-1% of a genome can be enriched to 60-80% in the preselected sample. In this workflow, the processing of information is not optimal. During preselection on the array, information is available about the genomic location of the DNA fragments, because they are specifically bound to probes that are spatially separated and can be identified. Nevertheless, the elution of the array is a one-chamber process, so that all selected fragments become mixed again. Consequently, after sequencing all reads have to be matched individually to a complete reference sequence, requiring a large computational effort. If one would be able to keep the genomic information from the preselection array into the sequencing reaction, this would significantly reduce computation requirements. The simplest way to retain this information is to do preselection and sequencing on the same spot on the same surface. Such methods are described in US application US2009/0117573. Since current sequencing technologies need amplification of every individual DNA fragment to obtain sufficient signal during sequencing, this amplification take places on the same spot. Based on the principle of bridge amplification technology, which is a surface-attached amplification that is for example used in Illumina's sequencing technology, a method is described to solve this. This can be performed on any solid surface (slides, carriers etc.) as long as individually amplified colonies can be discerned.

In these methods different hybridization, extension and ligation steps are used before sequencing can take place. More efficient and faster methods are still required.

SUMMARY OF THE INVENTION

Particular and preferred aspects of the invention are set out in the accompanying independent and dependent claims. Features from the dependent claims may be combined with features of the independent claims and with features of other dependent claims as appropriate and not merely as explicitly set out in the claims.

The present invention describes methods for amplification and sequencing of a captured target nucleic fragment directly on a capture probe spot. In these methods, a hairpin adaptor is ligated to a probe-target duplex, which can serve as an artificial bridge. The specific capture probe is then the single primer needed for bridge amplification.

The present invention relates to methods for amplifying a target nucleic acid comprising the following steps:
a) providing a support with a plurality of a nucleic acid capture probe, wherein the plurality of probes is immobilized to the support via the 5' end of the nucleic acid,
b) hybridizing a target nucleic acid to the capture nucleic acid probe to form a probe/target complex,
c) extending the capture nucleic acid with a polymerase wherein the target nucleic acid is used as template for the extension of the capture probe nucleic acid,
d) ligating the extended target/probe double stranded nucleic acid to a hairpin nucleic acid wherein the 5' end of the hairpin nucleic acid is ligated to 3' end of the extended probe and wherein the 3' and of the hairpin nucleic acid is ligated to the 5' end of the target nucleic acid,
e) allowing the 3' end of the target nucleic acid to bind to a further probe of the plurality of nucleic acid capture probes on the support,
f) extending the 3' end of the further probe by a polymerase,
g) amplifying the nucleic acid obtained in step f) by repeating steps e) and f).

In other particular embodiments, the polymerase in step c) has no terminal transferase activity or 3' to 5' proofreading exonuclease activity and wherein the hairpin nucleic acid forms a blunt ended stem. For example, the polymerase in step c) is Pfu (*Pyrococcus furiosus*) DNA polymerase.

In particular embodiments, the polymerase in step c) has a 3' terminal transferase activity, resulting in an overhang at the 3' end of the double stranded nucleic acid and wherein the hairpin nucleic acid has a 5' overhang, complementary to the 3' of the double stranded nucleic acid. For example, the polymerase in step c) is Taq (*Thermophilus aquaticus*) DNA polymerase, generating a 3' overhang of one adenine and the 5' overhang of the hairpin is one thymidine.

In a further preferred embodiment of the invention the polymerase in step c) is Klenow polymerase. This enzyme may be used in the presence of a single type of nucleotide generating a series of identical nucleotides along the captured fragment sequence.

In a further particularly preferred embodiment said single type of nucleotide is dTTP.

In yet another preferred embodiment the ligating of the extended target/probe double stranded nucleic acid to a hairpin nucleic acid of step d) is performed in the presence of PEG8000 in the ligation reaction. In a particularly preferred embodiment the ligating of the extended target/probe double stranded nucleic acid to a hairpin nucleic acid of step d) is performed in the presence of 5% PEG8000 (40 w/v).

In further particular embodiments, the double stranded blunt ended nucleotide acid is further treated with an enzyme having 3' terminal transferase activity.

In particular embodiments of methods of the present invention, the target nucleic acid is DNA.

In other particular embodiments of methods of the present invention, the hairpin nucleic acid comprises in its loop a sequence for a rare cutting restriction enzyme.

In yet other particular embodiments, the support is a planar support, comprising different distinct zones, each zone comprising a plurality of a different probe.

In particular embodiments of methods of the present invention, the support is a microcarrier, wherein the microcarrier comprises a plurality of one nucleic acid capture probe. Herein the microcarrier optionally comprises a detectable label, wherein the detectable label defines the sequence of the capture probe attached to the microcarrier.

In further particular embodiments of methods of the present invention, the amplification described above in step g) is followed by a sequence determination of the nucleic acid corresponding to the target nucleic acid and further comprises the step of correlating the determined sequence with the zone on the planar support or the label on the microcarrier.

BRIEF DESCRIPTION OF THE DRAWINGS

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

A) hybridization of target DNA; B) extension of capture probe; C) ligation of hairpin; D) denaturation and reannealing; E) bridge amplification; F) linearization; G) sequence determination.

Figure 1:
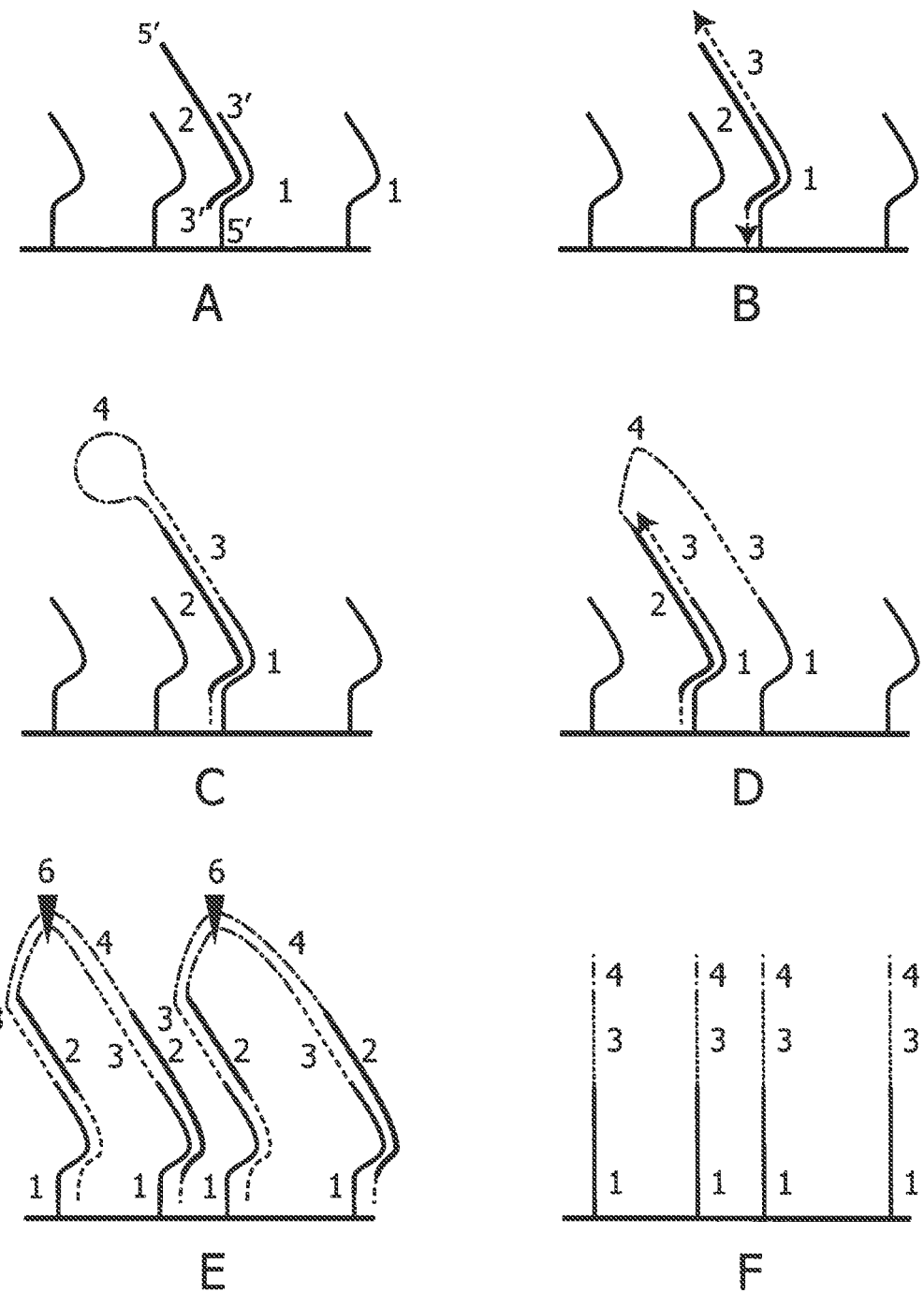
FIG. 1 shows an embodiment of methods described in the present invention.
Figure 1:
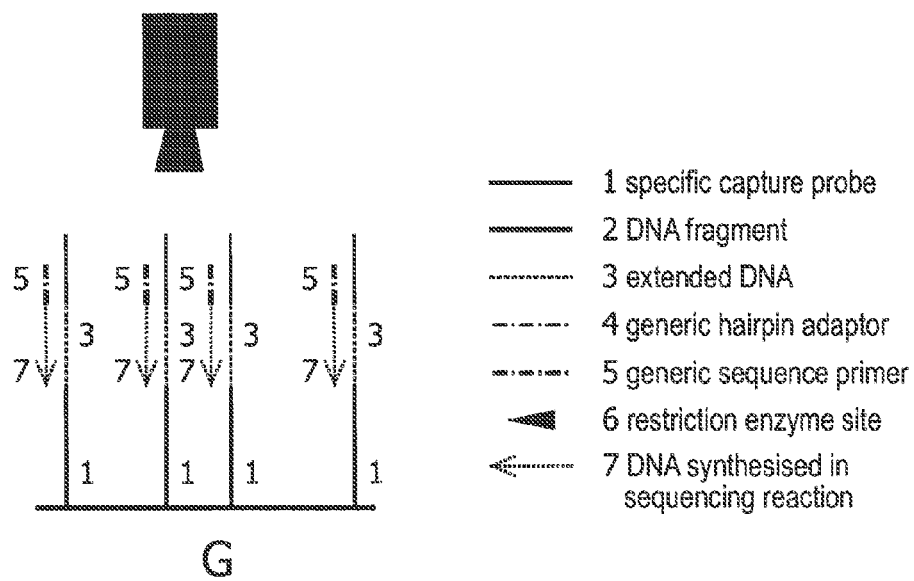
Figure 2:
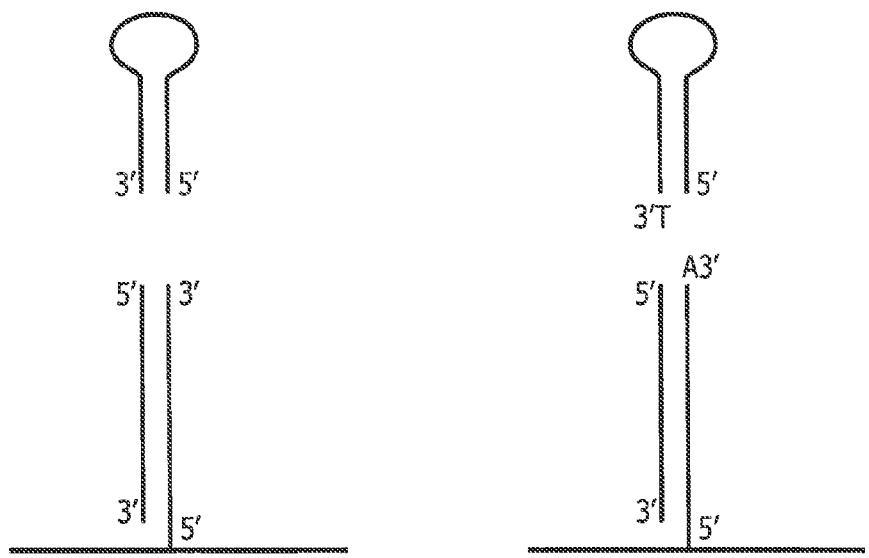

FIG. 2 shows two examples of an embodiment of the method step as depicted in panel C of FIG. 1.

The left part illustrates the extension with an enzyme without terminal transferase activity or with 3' to 5' exonuclease activity, wherein blunt ended double stranded DNA is generated for ligation with a blunt ended hairpin nucleic acid.

The right part illustrates the extension with an enzyme having 3' terminal transferase activity such as Taq DNA polymerase wherein double stranded DNA with a single adenine 3' overhang is generated for ligation with a hairpin nucleic acid with a single 5' thymidine overhang.

Figure 3:
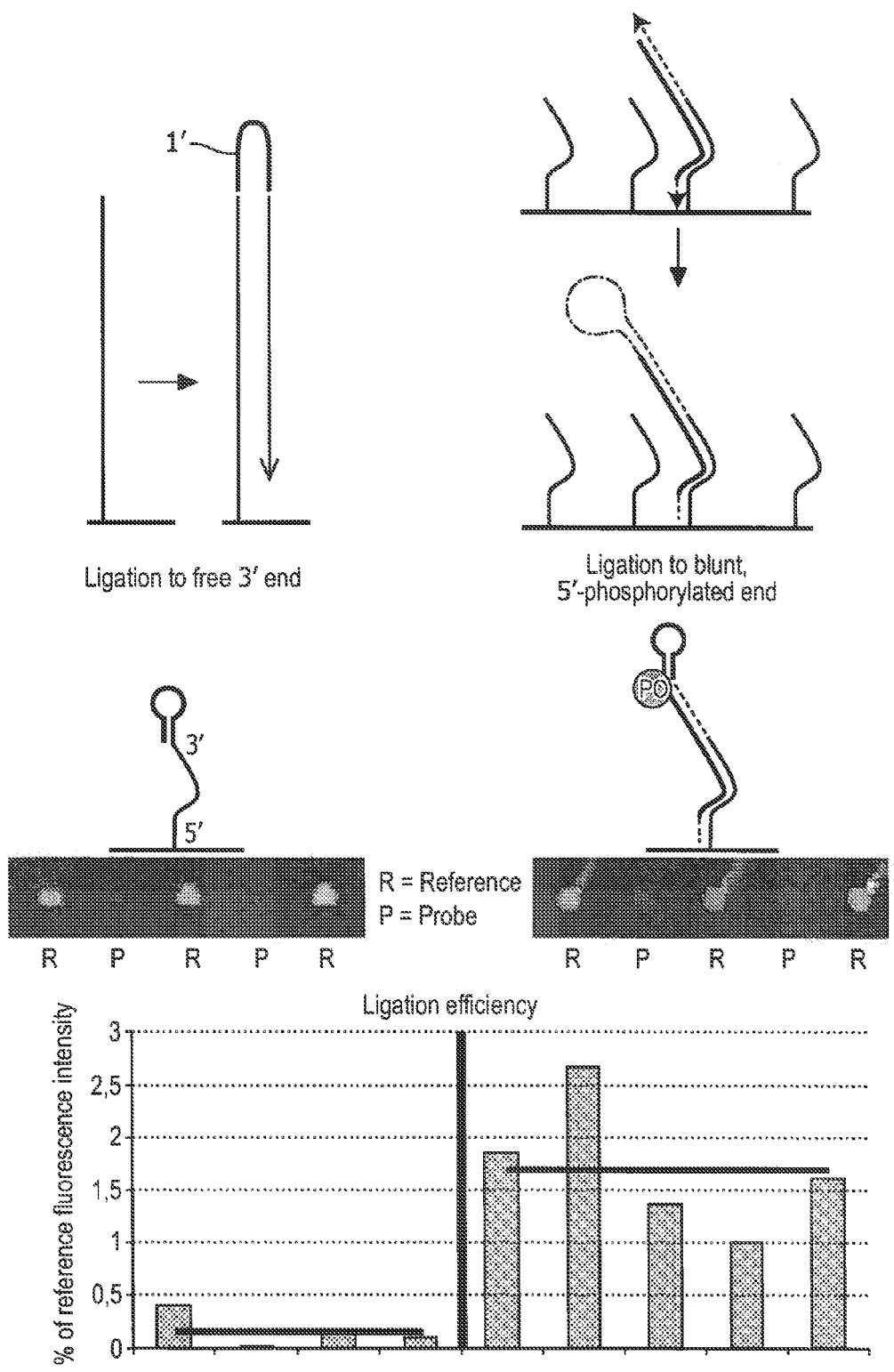

FIG. 3 shows a comparative example wherein the ligation efficiency of ligating a hairpin to a single stranded DNA (left part) is compared with the ligation efficiency of ligating a blunt hairpin to a blunt double stranded DNA.

Figure 4:
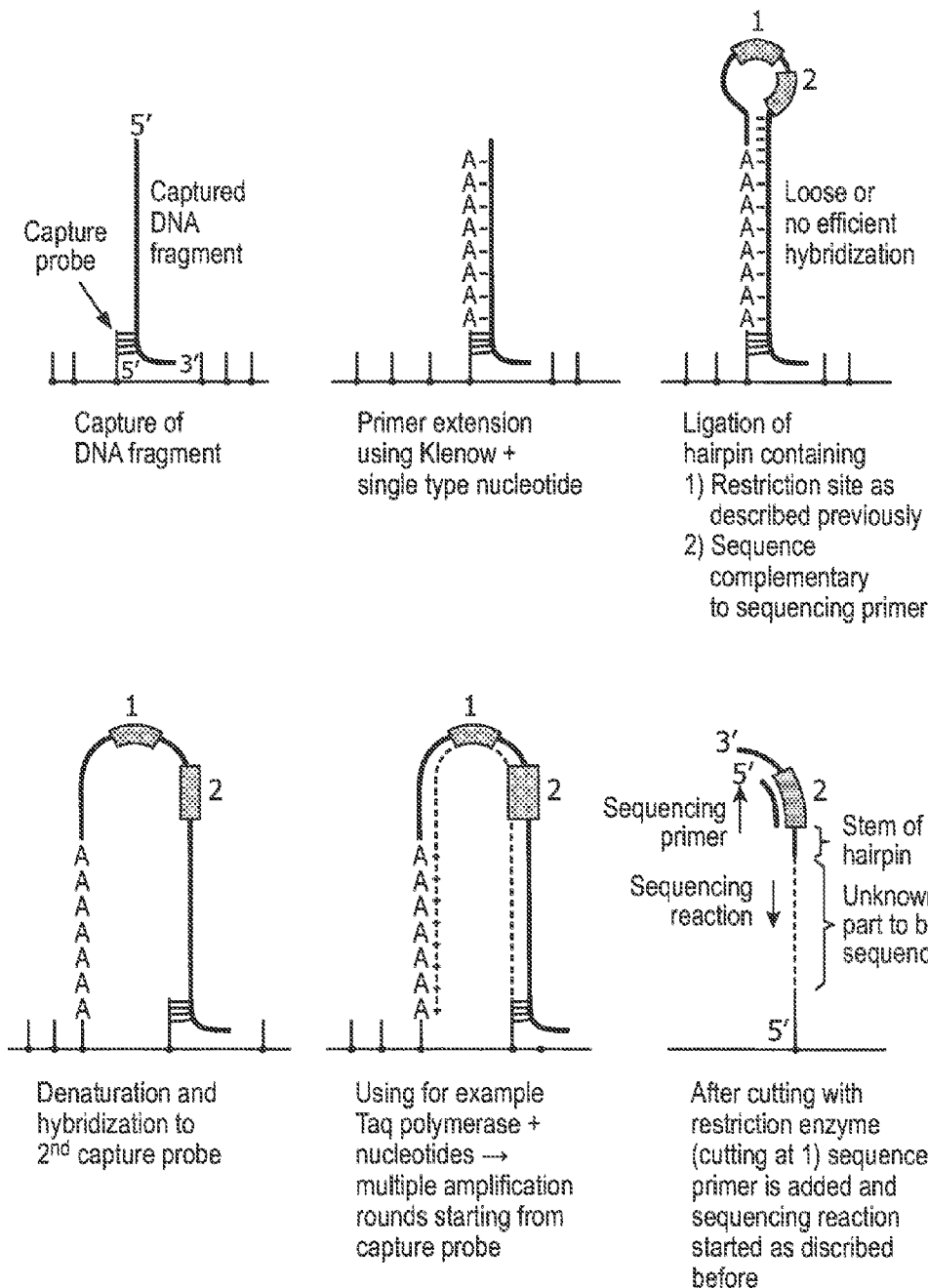

FIG. 4 illustrates the primer extension embodiment using Klenow polymerase and a single type nucleotide.

Figure 5:
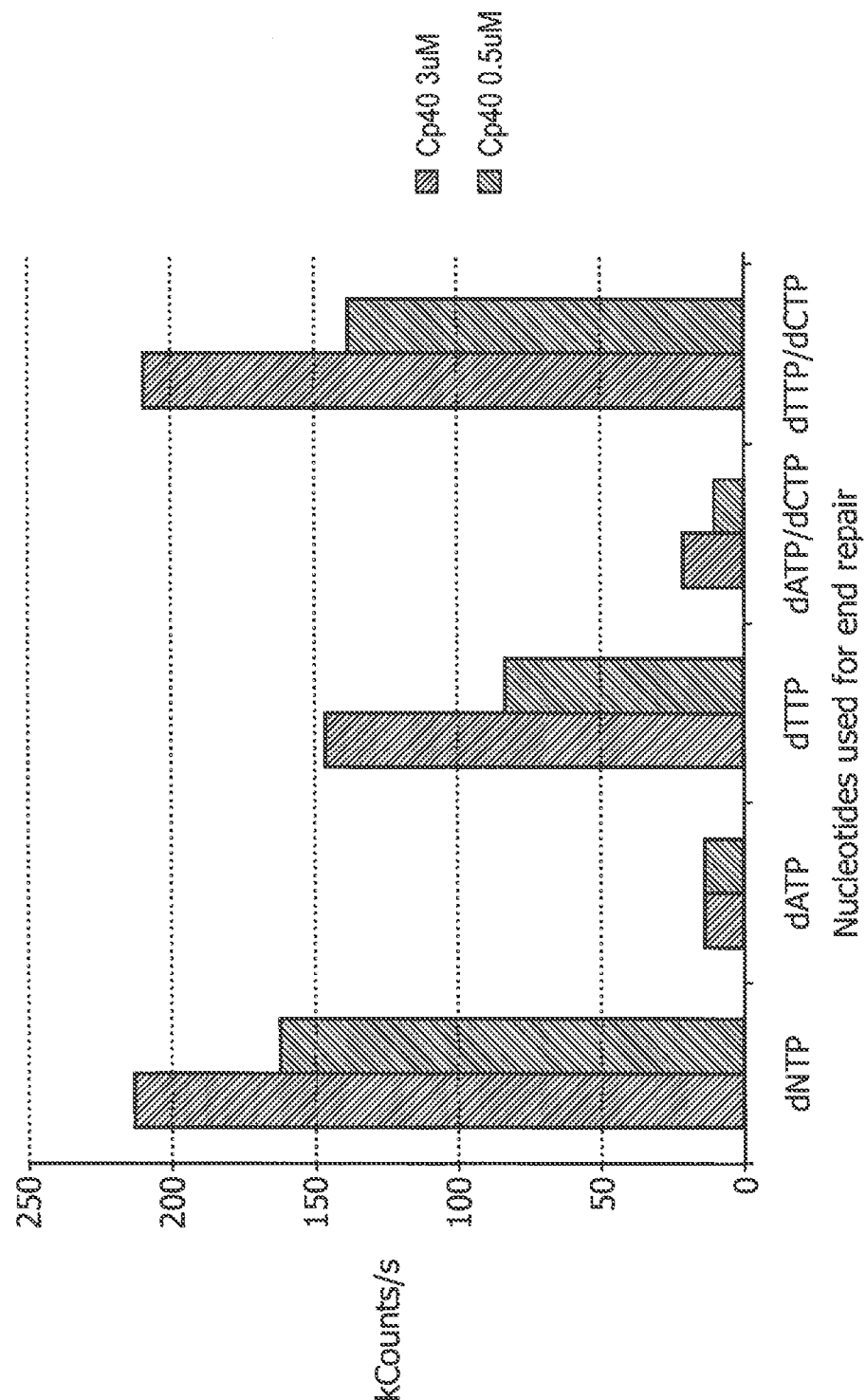

FIG. 5 shows fluorescence measurements after ligation with a fluorescently labeled hairpin using Klenow polymerase with different nucleotides.

Figure 6:
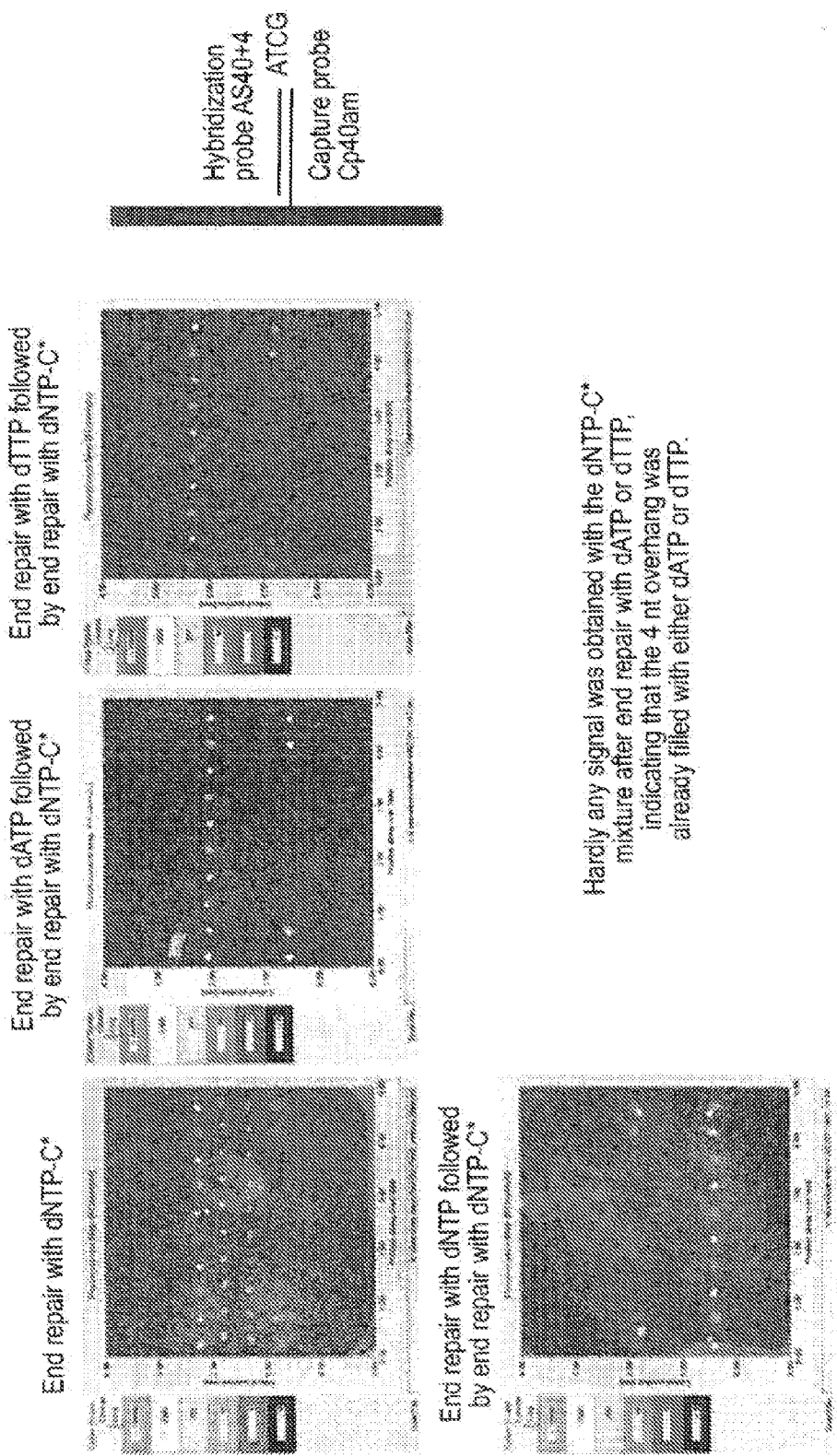

FIG. 6 shows experimental results obtained with a dNTP-C* mixture after end repair with dATP or dTTP, indicating that the 4 nt overhang was completely filled with dATP or dTTP. Fluorescence spots were obtained (two middle rows) for the reference (end repair with dNTP-C*), but when an initial end repair was performed with unlabeled ATCG, only A or only T nucleotides, no fluorescence signals were obtained from the dNTP-C* mixture. This indicates that ends are already completely filled in the initial end repair reaction irrespective of the nucleotides that were used for this reaction as no labeled C-nucleotides could be build in in the second reaction. In the different figures, the same reference signs refer to the same or analogous elements.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. These definitions should not be construed to have a scope less than understood by a person of ordinary skill in the art.

DETAILED DESCRIPTION OF THE EMBODIMENTS

Definitions

"Capture probe" or "capture oligonucleotide" refers to a nucleic acid which is attached to a solid support.

"Target DNA" or "target nucleic acid" refers to a nucleic acid which is obtained from a sample.

"Nucleic acid" refers to DNA as well as RNA, and may contain non-naturally occurring nucleotides or modifications.

"Proofreading" is used in the context of DNA polymerase enzymes with 3' to 5' exonuclease activity.

"Sticky" refers to an end of a double stranded nucleic acid wherein the 5' or the 3' end has an extension of one or more nucleotides and which do not form a base pair. This is in contrast to "blunt" wherein the terminal 5' nucleotide forms a basepair with the 3' terminal nucleotide.

"Hairpin nucleic acid" refers to an oligonucleotide with at the 3' end and at the 5' end sequences which are palindromic such that intramolecular basepairs are formed. These base paired sequences represent a stem. Between these palindromic sequences a stretch of nucleotides is present which remains unpaired, forming a loop. Loop and stem form a hairpin like structure. "(Micro)carrier" as used in the present invention relates to a solid particle with a diameter of between 0.1 and 1000 micrometer. Synonyms are "(micro)bead", "(micro)particle" or "(micro)sphere". The shape of the microbeads is not considered as a limitation of the invention.

The methods described in the present invention relate to the amplification of a target nucleic acid on a solid support.

Former amplification methods used primers in solution resulting in amplification products which are equally in solution. Recent amplification methods use primers which are attached on a support, such that the amplified products remain equally attached to the support. This has an advantage in multiplexing methods, because the different amplification products, obtained with different primers remain attached to the support. This allows correlating the amplified product with the position of the primer on the support.

Different ways can be envisaged to provide a primer on a support. In certain embodiments primers are attached to dedicated positions on an array. Modern immobilization techniques allow the attachment of up to millions of different primers on surfaces in the range of 1 to 100 µm².

Alternatively, primers can be attached to microparticles of glass, plastic or metal. In certain embodiments such particles are magnetic particles, allowing the manipulation in a magnetic field. Microparticles can be labeled with optical barcodes, graphic patterns, alphanumeric codes, colors (e.g. quantum dots) and the like to identify a microparticle and the primer that has been attached to it.

Methods as described in the present invention do not rely on the use of a pair of oligonucleotides as typically used in PCR reactions. In the present methods oligonucleotides are attached via the 5' end to the support. These probes are further referred to as "capture probes".

Nucleic acid capture probes as used in the present invention typically have length of about 15 to 150 nucleotides, e.g. between 20 to 1000 or 20 to nucleotides, to allow a specific binding to the envisaged target nucleic acid without or with low numbers of mismatches.

In a further step of the methods of the present invention a target nucleic acid is hybridized to a nucleic acid capture probe.

A plurality of probes of the same sequence is applied as a spot on a support such that thousands, tens of thousands, hundreds of thousands or millions of copies are present in each other vicinity to allow clonal amplification as explained further in this invention. Such spots can be circular, rectangular, elliptical, wedge-shaped in shape and have typically an area between 100 µm² and 10.000 µm², between 1 and 100 µm², or even between 0.1 to 1 µm². Depending on the size of the spots and their density on a support up to 100,000. 500, 000, 1, 2, 5, 10, 20, 50 or even 100 million different spots can be applied on a support, each spot comprising a plurality of the same target probe.

The target nucleic acid typically originates from genomic DNA and can be prepared by mechanical (e.g. sonication, shearing), chemical (with metal complexes or acidic treatment) or enzymatic (short time digest with common restriction enzymes or DNase and extensive digest with "rare cutter" enzymes) methods.

The average length of the genomic DNA fragment typically varies between 50 and 5000 bp, typically between 100 and 500, e.g. around 200 bp.

Hybridisation of genomic DNA to capture probes occurs under standard conditions, well known from micro-array techniques.

In an alternative embodiment, RNA (e.g. mRNA or miRNA) is hybridized to DNA capture probes. The capture probe is extended using enzymes with reverse transcriptase activity resulting in a DNA-RNA hybrid. Further steps are similar to those as described for DNA target and DNA capture probes.

A hybrid of target DNA and capture probe may comprise a part of capture probe which is still single stranded or alternatively may comprise a part of single stranded target DNA which extends beyond the 5' end of the capture probe. This however has no consequences for the further steps of the methods of the present invention.

In a further step of the methods of the present invention the capture probe is extended at its 3' end with a polymerase. Herein the target nucleic acid is used as a template for the extension of the capture probe.

Depending on the polymerase that is used two alternative embodiments are possible.

A) polymerase without terminal transferase activity or with proofreading activity. DNA polymerization with these DNA polymerase enzymes results in double stranded DNA with blunt ends, without overhang or recessive end at the 3' end. Enzymes within this class are for example Klenow polymerase and several polymerases which have polymerase activity below 95° C. such as pfu polymerase. As a result a blunt ended double stranded nucleic acid with the extended 3' end of the capture probe and the original 5' end of the target DNA is generated.

As explained above, depending on the type of hybrid that has been formed, extension of the 3' end of the target DNA may also occur.

Extended blunt ended DNA as obtained with these enzymes can be used without further steps in a blunt double stranded ligation. In this embodiment a blunted hairpin is ligated to the extended target/probe nucleic acid wherein the 5' end of the hairpin nucleic acid is ligated to 3' end of the extended target probe nucleic acid and wherein the 3' end of the hairpin nucleic acid is ligated to the 5' end of the target nucleic acid (see FIG. 2, left part).

B) polymerase with terminal transferase activity and without proofreading activity.

DNA polymerases such as Taq polymerase, do not have the above mentioned exonuclease activity but have a 3' terminal transferase activity, whereby additional overhanging nucleotides are incorporated. Using Taq polymerase a 3' overhang of one adenine is obtained.

Accordingly DNA polymerization with these polymerases results in a sticky end. According to these particular embodiments a hairpin nucleic acid is used, which beyond its stem has a 5' overhang, complementary to the 3' overhang generated by the DNA polymerase (see FIG. 2, right part).

In embodiments wherein Taq polymerase is used and a 3' overhang of one adenine is obtained, a hairpin nucleic acid with a 5' overhang of thymidine is ligated. This ligation is similar to the so called TA cloning wherein PCR products are cloned into vectors with a 5' T overhang (TA cloning kit of Invitrogen).

The ligation efficiency of such single nucleotides is considered to be more efficient than the ligation of blunt ended double stranded DNA.

However, apart from the advantage in cloning DNA with sticky ends, enzymes such as Taq polymerase have the disadvantage that the error rate of polymerization is considerably higher compared to proofreading enzymes.

In sequencing projects, the improved ligation efficiency obtained with sticky end, may compensate for the error rate of DNA polymerase, since the chances of ligating target DNA occurring with a low frequency within a sample will increase.

In methods wherein the accuracy of the sequence is more critical such as genetic diagnosis, the proofreading aspect of a polymerase may prevail over the terminal transferase activity of the other type of polymerase.

In yet further embodiments, which however require additional method steps, the advantages of both enzymes can be exploited. Herein the extension of the capture probe, using the target DNA is performed with a proofreading enzyme such that a sequence is generated with a minimal amount of errors. The blunt ended double stranded generated nucleic acid is further treated with a polymerase with terminal transferase activity and the appropriate dNTP, resulting in a sticky end with a 3' overhang allowing a sticky end ligation.

In a further embodiment the polymerase to be used in step c) may be Klenow polymerase. This enzyme may be used in the presence of a single type of nucleotide, e.g. dATP, dGTP, dCTP, dTTP. Thereby a series of identical or similar nucleotides along the captured fragment sequence may be generated. It is preferred to use single nucleotides such as dATP and dTTP. It is most preferred to use Klenow polymerase together with dTTP.

In further specific embodiments of the present invention for the subsequent ligation of the hairpin structure, results may be improved when a sequence-specific nucleotide complementary to the last nucleotide of the captured fragment is added. The sequence specific nucleotide may be A, G or C Thus, in specific embodiments, a Klenow polymerase may be used together with a combination of dTTP and dATP, or a combination of dTTP and dGTP, or a combination of dTTP and dCTP.

In another embodiment the ligating the extended target/probe double stranded nucleic acid to a hairpin nucleic acid of step d) is performed in the presence of a high molecular weight polymer molecule. Particularly preferred is the use of PEG8000 in the ligation reaction. It is particularly preferred to ligate the extended target/probe double stranded nucleic acid to a hairpin nucleic acid of step d) in the presence of about 2% to 15% of PEG8000 (40 w/v), more preferably in the presence of about 3% to 7% of PEG8000 (40 w/v), even more preferably in the presence of about 5% of PEG8000 (40 w/v). In these steps wherein the extension by a polymerase is immediately followed by a ligation with a hairpin nucleic acid, there is a significant difference with prior art methods as described in e.g. in the '573 application of Affymetrix. In the prior art the ligation of a hairpin is always followed by a further extension of the hairpin nucleic acid. The possibility to ligate a hairpin (blunt or with 5' overhang) such that a double stranded nucleic acid is obtained which requires no further extension, has not been appreciated or envisaged in the prior art.

This difference allows shortening significantly the time needed to perform all steps of the method, because there is no need for an additional extension step after the ligation reaction. Furthermore it has been demonstrated that the yield of ligation using a hairpin nucleic acid to double stranded nucleotide nucleic acids, is higher compared to the yield of ligation with a hairpin to a free, single stranded 3' end. In this way, the sequencing project will reveal a higher fraction of the target DNA that is present in a sample.

After ligation with the hairpin nucleic acid, methods as described in the present invention result in a continuous sequence beginning on the support at the 5' end of the capture probe, along the original capture probe sequence, the extended capture probe sequence, the sequence originating from the hairpin, and the target DNA sequence until the 3' end of the target sequence, as obtained in the prior art. Similar as in the prior art, this sequence is suitable for bridge amplification and subsequent sequence determination.

Bridge amplification is known in the art from e.g. U.S. Pat. No. 6,300,070, Westin et al. (2000) *Nat. Biotechnol.* 18, 199-204, Walker et al. (1992) *Proc Natl Acad Sci USA* 89; 392-396, Shapero et al., (2001) *Genome Res.* 11, 1926-1934 and Ju et al. (2006) *Proc Natl Acad Sci USA*. 103, 19635-19640. Herein, one end of the target to be amplified is tethered via a first probe and the other end is free to hybridize to a second probe that is physically close enough to the first probe so that hybridization can occur. The distance within which a second probe can be located will be determined by the length of the target.

The sequence determination can be performed on the surface itself. Alternatively, DNA is eluted from the surface and sequenced.

Surfaces of planar supports or microcarriers as used in the present invention are made of a material or functionalised with a material, which allows the binding of oligonucleotides to the surface. The coupling of oligonucleotides to surfaces is well known in the art. This coupling can be irreversible or reversible (e.g. by thiol, acid, or alkali labile groups).

In certain embodiments the microparticles have a size and shape that allows the manipulation of particles in a microfluidic device. Microcarriers can have an electric charge to allow the manipulation in an electric field.

In other embodiments the carriers are magnetic or magnetisable particles, which allows the manipulation, rotation or positioning in a magnetic field.

In other embodiment the particles are positioned and or manipulated using optical tweezers.

When microcarriers are used they may comprise label or code, which allows the identification of an individual carrier within a plurality of carriers. The encoding of carriers has been known for a long time in multiplexing methods wherein carriers are functionalised with chromophoric (e.g. fluorescent) labels with different absorption or emission maxima. For example Luminex (Austin, Tex.) provides microcarriers, comprising different concentrations of two dyes resulting in 100 different blends. In methods in accordance with the present invention, (and this in contrast to microarray techniques), a capture probe is not identified by its co-ordinates on a matrix but is identified by the code or the nature of the microcarrier. As a consequence, encoded microcarriers with capture probes can be present in solution in at least one step or even in all steps of the described methods.

A higher complexity of encoding is achieved by using e.g. quantum dots, allowing a complexity of up to 1 million using 10 intensity levels and 6 colours.

Different type of barcodes are known in the art and include electronic barcode using radio frequency tags, laser etched barcodes, metallic nanorods (reviewed in Jain K. (2003) *Expert Rev Mol Diagn.* 3, 153-161; Lehmann (2002) *Nature Materials* 1, 12-13; Braeckmans et al. (2002) *Nature review, drug discovery* 1, 447-448). In metallic nanorods, the barcode is obtained by the different materials, which are used to make the carriers.

In particular embodiments, the barcode is a miniaturised readable code of any geometry, design, or symbol that can be written on the surface or even within and read on the microcarriers. For example, the codes may be written as numbers or letters, or as codes in the form of symbols, pictures, bar codes, ring codes, or three-dimensional codes. Ring codes are similar to bar codes, except that concentric circles are used rather than straight lines. Alternatively two-dimensional patterns are used to represent a code.

In a particular embodiment a high complexity is obtained using barcodes which are written on or within a microcarrier via partial photobleaching of fluorescent particles. This process allows writing symbols, lines, numbers and the like on particles. A line pattern can be written on a microcarrier such that a barcode pattern is obtained that can be read by optical devices. The spatial selective photobleaching of microcarriers is described in detail in Braeckmans et al. (2003) *Nature Materials* 2, 169-173 and Serveaux (2007) *Langmuir.* 25 10272-10279. A barcode can be written several times on a microcarrier, allowing to read the barcode irrespective of the orientation of the microcarrier.

In a further particular embodiment the microcarrier comprises also magnetic material, which allows magnetic manipulation of the particles. The manufacture of such particles is described in detail in patent applications WO2007115815, EP1346224 and WO0063695.

For a typical targeted sequencing effort for a clinical diagnosis, sequencing of up to 1000 genes is needed. For such direct capture-sequencing approach, dense tiling of probes up to each base is necessary, because the reaction will not run if there is a mutation in the fragment complementary to the 3' end of the capture probe. That means that for sequencing of 100 genes of average 1000 bases each, 100×1000×2 strands=200,000 different probes are needed, for sequencing 1000 genes 2,000,000 probes are needed.

For proper and quantitative mutation detection, 200× or more sequencing coverage of each base of each strand may be required. Supposing 10 bases can be sequenced on each read and 80% of reads are lost because of errors, then 1000 DNA fragments covering each base need to be captured. This can be divided over 10 different overlapping probes, so 100 captured fragments per probe could be sufficient.

The Illumina sequencing procedure is able to detect 0.1-1 amplified colonies per $\mu m^2$ thus for 100 amplified DNA fragments a surface area of 100-1000 $\mu m^2$ is needed, which is within the size range of microarray probe spots (6-36 $\mu m$ Ø). For efficient bridge amplification the density of capture probes may need to be 100-1000-fold higher than the fragment concentration (8), but 10-1000 probes per $m^2$ is within the possibilities of most microarray production technologies (U.S. Pat. No. 7,115,400; Kawasaki E. (2006) *J. Biom. Techniques* 17, 200-206)

Other arrangements of the systems and methods embodying the invention will be obvious for those skilled in the art.

It is to be understood that although preferred embodiments, specific constructions and configurations, as well as materials, have been discussed herein for devices according to the present invention, various changes or modifications in form and detail may be made without departing from the scope and spirit of this invention.

EXAMPLES

Example 1

An example presenting a typical embodiment of the present invention as applied on a sample of genomic DNA is discussed below. The different steps herein describe embodiments wherein a DNA polymerase without terminal transferase activity is used.

1.1. Capture of Target Fragment on the 5' Bound Capture Probe on the Array Surface. (FIG. 1A)

Captured fragments should be sufficiently spaced, so that after amplification they can be imaged as individual colony in a sequencing reaction. Fragment lengths of target DNA are chosen longer than capture probes, so that 5' overhang of the fragment can be generally assumed. Apart from perfect matches between capture and target nucleic acids, capture probes may also be designed to allow for specific binding of DNA fragments that are slightly mutated. In the latter case such capture probes typically require a length of around 60 nucleotides. For the hybridization of the target DNA to the capture probe, standard hybridization buffers, conditions and post-hybridization washing conditions can be used as known in the art. If the hybridization with mutated target nucleic acids is envisaged stringency conditions are adapted accordingly.

1.2. Extension of the Capture Probe (FIG. 1B)

The 3' end of the hybridized capture probe is extended such that a blunt end of the target DNA/capture probe duplex is formed.

This can be done by standard end repair enzyme mixes that contain at least a 5'-3' polymerase and a 5' kinase to phosphorylate the 5' end of the duplex for further ligation to other nucleic acid fragments. End repair protocols are commonly used for fragmented DNA. In this procedure, the captured target may also be extended on its 3' end, but has not consequence on the further steps in the method.

In order to allow the extension of the capture probe a free hydroxyl group at the 3' end is required. For this reason capture probes are in the methods of the invention attached with their 5' end to the support. 5' end of attachment is typically achieved by direct synthesis, by spotting individual oligonucleotides, followed by chemical covalent attachment of 5' end or by an inversion of synthesized probes on the surface (Kwiatkowski M. et al. (1999) *Nucleic Acids Res.* 27, 4710-4714).

1.3. Ligation of a Hairpin Adaptor to the Probe/Fragment Duplex. (FIG. 1C)

The blunt end ligation of hairpin adaptors is known in the art from e.g. Ref. 7. Double stranded DNA hairpin adaptors have at least a stem (doublestranded part) of at least 6-7 basepairs and a loop of a similar number of bases to allow folding.

For the purpose of the methods of the present invention, a hairpin molecule with a longer length is generally used, such that a specific primer binding site (typically about 15-25 nucleotides) can be included (as further explained in step 7) of about 20 nucleotides, as well as a restriction site that is not commonly found in genomes, such as I-SceI (step 5, 18 nucleotides) Other enzymes with similar properties can be commercially obtained. In addition, a total length of 200 to 500 nucleotides of the bridging molecule (probe+extension+ hairpin+target) is needed to allow bridge amplification (as further explained in step 4). That would mean that with 50-200 bp target and probe+extension lengths a hairpin of around 100 nucleotides is required.

One and the same hairpin nucleic acid can be used to ligate the different extended target DNA/capture probe nucleic acids.

1.4. Denaturation and Subsequent Hybridization to a Neighboring Capture Probe, and Bridge Amplification (FIG. 1D).

An extended probe/target complex with a hairpin, can, after denaturation, hybridize back to itself. In the methods of the present invention, the number of neighboring target probes attached to the support is that high that after denaturation, it is more likely that the DNA sequence originating from the target DNA will bind to a neighboring capture probe rather than to the complementary part of the sequence originating from the capture probe nucleic acid.

These complexes are amplified by "so-called "bridge amplification" using standard thermocycling with a thermostable polymerase or by isothermal amplification.

The annealing step of in bridge amplification may require a longer duration, compared to PCR reaction wherein primers of about 20 to 40 nucleotides are used, because the probe-primers are longer than such standard PCR primers. For efficient bridge amplification, a total bridge length of 200-500 bases is generally used. This can be achieved by adapting the lengths of the capture probes, the DNA fragments as well as the hairpin molecule.

The above described denaturation, hybridization and extension step is repeated.

10 to 60 cycles of amplification are generally needed to create a well-detectable colony.

After the amplification PCR reagents are then washed away with standard buffers.

1.5. Cleavage of Duplex Bridges (FIG. 1E)

The double stranded DNA that is obtained after the amplification step is cleaved with a restriction enzyme at a specific recognition site within the sequence originating from the hairpin adaptor. Typically restriction enzyme recognition sites are chosen that rarely occur in genome sequences. Enzymes such as I-SceI with large recognition sites are suitable for this purpose.

1.6. Denaturation of Cleaved DNA (FIG. 1F)

The cleaved duplexes are denatured (by heat or chemically) and the DNA that is not attached to the surface is washed away with standard buffers. This results in attached molecules consisting of capture probe nucleic acid (solid line at bottom), an unknown nucleic acid complementary to the target DNA (dotted line) and a part of the hairpin adaptor nucleic acid (solid line on top line).

1.7. Sequencing of Unknown Target DNA (FIG. 1G)

Using a generic primer complementary to the hairpin adaptor, a sequencing reaction is performed with any suited sequencing chemistry, such as base-by-base addition of reversible terminated nucleotides.

Example 2

Experimental Details of Procedure 2.1. Hybridization of Target DNA to Capture Probe In house spotted arrays on commercial aminosilane slides with spots of capture probes of 58 nucleotides length have been used for the hybridization of a target DNA of 40 nucleotides, all complementary to the capture probe.

The array was hybridized with a 10 pM or 10 nM solution of the target DNA, labeled at the 5' end with an Atto700 fluorescent label.

A control was performed with spots of a reference probe (which is a non-binding piece of DNA with an Atto700 label) and of a probe with an irrelevant sequence (non-binding probe), unable to hybridize with the target DNA.

The hybridization was performed for 30 min at 50° C. with the target DNA in 3×SSC; 0.1% SDS. For the hybridization of genomic DNA (with fragment length of 50-5000 bp) hybridization for a longer duration (1-64 hours) is appropriate.

The hybridized probes were washed 3×5 min with 1×SSC; 0.2% SDS at room temperature.

Detection of the label shows besides the reference probe that the target DNA has bound to the capture probes, whereas the non-binding probe was not detected.

2.2. Extension Repair

A further hybridization experiment was performed using the conditions described above, and similar spotted arrays with capture probes (without fluorescent labels) references and non-binding probes:

10 nM of a target DNA of 62 nucleotides with 40 nucleotides complementary to the capture probe and a 5' overhang of 4 nucleotides, comprising a guanine residue.

0 nM of a target DNA of 58 nucleotides with 40 nucleotides complementary to the capture probe and without a 5' overhang.

After the hybridization the capture probe was elongated during 30-60 min 37° C. with Klenow enzyme and dATP, dGTP, dTTP and Cy5-labeled dCTP in Klenow buffer+0.5% BSA. The reaction was stopped by washing 3×5 min with 1×SSC; 0.2% SDS.

The Cy5 fluorescent label was only detected with the target probe having the 5' overhang. The probe without the overhang, which forms a blunt ended complex, had not nucleotides incorporated (Both probes with and without overhang have a 18 bp tail at their 3' end that is not complementary to the capture probe, which blocks incorporation of nucleotides at this side of the molecule).

2.3. Adaptor Ligation.

The experiment as described above is repeated with unlabeled nucleotides and 500 nM of a 5' phosphorylated hairpin oligo having either a loop of 20 nucleotides and a stem of 6 basepairs or a loop of 28 nucleotides and a stem of 33 basepairs is ligated as follows:

Phosphorylation of the probe-target duplex for 45-60 min 37° C. with T4 kinase in ligase buffer+0.5% BSA Ligation with T4 ligase and hairpin oligo in ligase buffer+0.5% BSA at room temperature.

Non-ligated hairpin is removed by washing for 3×5 min with 1×SSC; 0.2% SDS

The hairpin contains in its loop region an internal Atto700 label to allow the detection of ligated hairpin and to assess the yield of the ligation.

2.4. 1$^{st}$ Step of Bridge Amplification

As a proof of principle, the experiment as described above is repeated with unlabeled hairpins using 10 nM of the target DNA (40 nucleotides complementary with capture probe, no overhang).

Hereafter a first round of bridge amplification is performed as follows: The duplex with the ligated hairpin is denatured for 3 min at 95° C. in 3×SSC; 0.1% SDS and rehybridize 30 min at 50° C.

Second strand synthesis is performed for 30-60 min at 37° C. with Klenow enzyme and dATP, dGTP, dTTP and Cy5-labeled dCTP in Klenow buffer+0.5% BSA. Detection of label proofs that second strand synthesis has occurred.

Example 3

Experimental Details of Alternative Adaptor Ligation Step

The experiment described in Example 2 (See Above) was repeated with several modifications:

Instead of SAL-slides a Nexterion P MPX-16 slide (SCHOTT) in combination with a superstructure (Schott) was used. This slided yielded a very low background, good signal-background ratio; furthermore, no blocking was needed.

Correspondingly, a SCHOTT washing protocol was carried out comprising the following steps:

Wash Buffer 1 (PBST, 2.0%): PBS with 2.0% Tween® 20: since the slide (including superstructure) was completely immersed in the buffer solution, removing the seal of the superstructure in the buffer, resulted in an immediate inflow of the washing buffer.

Wash Buffer 2 (PBST, 1.0%): PBS with 1.0% Tween® 20: 5 min with shaking

Wash Buffer 3 (PBST, 0.5%): PBS with 0.5% Tween® 20: 2 min with agitation

Wash Buffer 4 (PBST, 0.1%): PBS with 0.1% Tween® 20: 2 min with agitation

PBS: 2×2 min with agitation

End repair of the nucleic acids and phosphorylation reaction were carried out simultaneously for about 1 h at 37° C. The end repair for 4 nucleotides could be performed in minutes.

Subsequently, the ligation reaction was carried out by adding 5% PEG8000 (40% w/v) to the reaction solution. The ligation was performed at room temperature for about 1 h, 2 h, or 4 h or overnight. The experiment demonstrated that a ligation at room temperature for about 2 h is sufficient to yield good ligation results.

Example 4

Extension Repair

A further hybridization experiment was performed using the conditions described in Exmaples 2 and 3, and similar spotted arrays with capture probes (without fluorescent labels) references and non-binding probes:

10 nM of a target DNA of 74 nucleotides with 40 nucleotides complementary to the capture probe and a 5' overhang of 16 nucleotides, comprising a guanine residue. After the hybridization the capture probe elongated during 30-60 min 37° C. with Klenow enzyme and dATP or dTTP or a mixture of dATP and dCTP or dTTP and dCTP in Klenow buffer+ 0.5% BSA. As a reference an elongation reaction containing all four nucleotides was performed. During the elongation reaction also a phosphorylation reaction was performed to phosphorylate the probe-target duplex using T4 kinase in kinase buffer+0.5% BSA. Ligation was performed with T4 ligase and hairpin oligo in ligase buffer+0.5% BSA and 5% PEG8000 (40 w/v) at room temperature for 2 hours.

Non-ligated hairpin is removed by using the Schott washing protocol The hairpin contains in its loop region an internal Atto700 label to allow the detection of ligated hairpin and to assess the yield of the ligation. As ligation can only occur on blunt ends, detection of label proofs that the 16-nucleotide overhang is completely filled with nucleotides.

As can be seen in FIG. 5, ligation occurred when the normal nucleotide mixture (A, C, T and G) was used for end repair (reference), no ligation occurred after end repair with only A nucleotides and less optimal ligation occurred after end repair with only T nucleotides.

For this specific sequence ligation after end repair with only T nucleotides improved up to the level of the reference reaction, when C nucleotides were added to the end repair reaction. Thus, for the subsequent ligation of the hairpin structure, results may be improved when a sequence-specific nucleotide is added, e.g. the complementary C to the last nucleotide as in the case of the present Example. For other sequences the final nucleotide may be different and, in consequence, a different nucleotide may be added to a reaction solution comprising the T nucleotide.

The example indicates that it is possible to do a primer extension step with Klenow polymerase and only T nucleotides or combinations comprising T nucleotides to prevent self hybridization during bridge amplification.

Example 5

Extension Repair with ATCG, Only A or Only T Nucleotides

Another negative control experiment was performed in which fragment sequences with a 4 nucleotide overhang were hybridized to capture probes printed on a glass slide. An end repair reaction was performed using Klenow polymerase in the presence of; respectively, all four nucleotides (A, T, C and G), only A nucleotides or only T nucleotides. After this end repair reaction, a second en repair reaction was performed using a nucleotide mixture containing all four nucleotides of which the C-nucleotide was fluorescently labeled. A fluorescent signal after this second end repair reaction would indicate that not all ends were completed in the first reaction and thus that the end repair reaction with only A or T nucleotides did not work (see also FIG. 6), as was expected. This result thus confirms the experimental findings described in Example 4. The example indicates that it is possible to do a primer extension reaction using Klenow polymerase and either ATCG, only A or only T nucleotides.

Example 6

Comparative Example

The efficiency of the ligation of a blunt ended hairpin (stem of 6 basepairs and a loop of 20 nucleotides) to a single stranded capture probe was compared with the ligation of the same hairpin nucleic acid to a hybridized and therefore double stranded capture probe (FIG. 3). According to measured fluorescence signal (as a % of reference probe signal to correct for differences between scans) and averaged over several experiments, the ligation to the double-stranded probe is ~10-fold more efficient than ligation to a single-stranded probe.

The invention claimed is:

1. A method for amplifying a target nucleic acid comprising the steps of:
    a) providing a support with a plurality of a nucleic acid capture probe, wherein said plurality of probes is immobilized to the support via the 5' end of the nucleic acid,
    b) hybridizing a target nucleic acid to the capture nucleic acid probe to form a probe/target complex,
    c) extending the capture probe nucleic acid with a polymerase wherein the target nucleic acid is used as template for the extension of the capture probe nucleic acid,
    d) ligating the extended target/probe double stranded nucleic acid to a hairpin nucleic acid wherein the 5' end of the hairpin nucleic acid is ligated to 3' end of the extended probe and wherein the 3' end of the hairpin nucleic acid is ligated to the 5' end of the target nucleic acid,
    e) allowing the 3' end of the target nucleic acid to bind to a further probe of said plurality of nucleic acid capture probes on said support,
    f) extending the 3' end of said further probe by a polymerase,
    g) amplifying the nucleic acid obtained in step f) by repeating steps e) and f).

2. The method according to claim 1, wherein the polymerase in step c) has a 3' to 5' proofreading exonuclease activity and wherein the hairpin nucleic acid forms a blunt ended stem.

3. The method according to claim 1, wherein the polymerase in step c) is Pfu (*Pyrococcus furiosus*) DNA polymerase.

4. The method according to claim 1, wherein the polymerase in step c) has a 3' terminal transferase activity, resulting in an overhang at the 3' end of the double stranded nucleic acid and wherein the hairpin nucleic acid has a 5' overhang, complementary to the 3' of the double stranded nucleic acid.

5. The method according to claim 1 wherein the polymerase in step c) is Taq (*Thermophiles aquaticus*) DNA polymerase, generating a 3' overhang of adenine and wherein the 5' end of the hairpin nucleic acid has an overhang of thymidine.

6. The method according to claim 1, wherein the polymerase in step c) is Klenow polymerase, which is used in the presence of a single type of nucleotide generating a series of identical nucleotides along the target nucleic acid hybridized to the capture nucleic acid probe.

7. The method according to claim 6, wherein said single type of nucleotide is dTTP.

8. The method according to claim 1, wherein said ligating the extended target/probe double stranded nucleic acid to a hairpin nucleic acid of step d) is performed in the presence of PEG8000 in the ligation reaction.

9. The method according to claim 1, wherein the target nucleic acid is DNA.

10. The method according to claim 1, wherein the hairpin sequence comprises in its loop a sequence for a rare cutting restriction enzyme.

11. The method according to claim 1, where the support is a planar support, comprising different distinct zones, each zone comprising a plurality of a different probe.

12. The method according to claim 1, wherein the support is a microcarrier, wherein said microcarrier comprises a plurality of one nucleic acid capture probe.

13. The method according to claim 12, wherein the microcarrier comprises a detectable label and wherein the detectable label defines the sequence of the capture probe attached to the microcarrier.

14. The method according to claim 1, wherein the amplification in step g) of claim 1 is followed by a sequence determination of the nucleic acid corresponding to the target nucleic acid.

15. The method according to claim 14, wherein the sequence determination is performed on a planar support.

* * * * *